United States Patent
Caspary (10) Patent No.: US 9,855,399 B2
(45) Date of Patent: Jan. 2, 2018

(54) AIR HUMIDIFIER WITH BOIL-OVER PROTECTION

(71) Applicant: Draëger Medical GmbH, Lübeck (DE)

(72) Inventor: Renè Caspary, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 862 days.

(21) Appl. No.: 14/104,015

(22) Filed: Dec. 12, 2013

(65) Prior Publication Data

US 2014/0171728 A1 Jun. 19, 2014

(30) Foreign Application Priority Data

Dec. 13, 2012 (DE) .................. 10 2012 024 401

(51) Int. Cl.
| | |
|---|---|
| *A61G 11/00* | (2006.01) |
| *A61M 16/10* | (2006.01) |
| *A61M 16/16* | (2006.01) |
| *F22B 1/28* | (2006.01) |
| *A61M 16/06* | (2006.01) |
| *A61M 16/00* | (2006.01) |

(52) U.S. Cl.
CPC ...... *A61M 16/109* (2014.02); *A61M 16/0627* (2014.02); *A61M 16/16* (2013.01); *F22B 1/284* (2013.01); *A61G 11/00* (2013.01); *A61M 16/0066* (2013.01); *A61M 16/101* (2014.02); *A61M 16/107* (2014.02); *A61M 16/108* (2014.02); *A61M 16/1055* (2013.01); *A61M 2016/1025* (2013.01); *A61M 2205/3368* (2013.01); *Y10T 29/49396* (2015.01)

(58) Field of Classification Search
CPC ...... A61G 10/00–10/14; A61G 11/00–11/009; A61G 2203/46; F24F 6/02–6/025; A61M 16/16–16/168; B60H 3/022
See application file for complete search history.

(56) References Cited

U.S. PATENT DOCUMENTS

| | | | | | |
|---|---|---|---|---|---|
| 2,124,482 | A | * | 7/1938 | Blair | F24F 6/025 261/142 |
| 4,025,590 | A | * | 5/1977 | Igich | A61J 1/00 128/203.12 |
| 5,242,375 | A | * | 9/1993 | McDonough | A61G 11/00 600/22 |
| 5,539,854 | A | * | 7/1996 | Jones | A61G 11/00 392/403 |
| 5,792,041 | A | * | 8/1998 | Kobayashi | A61G 11/00 600/22 |

(Continued)

FOREIGN PATENT DOCUMENTS

| | | |
|---|---|---|
| CN | 2080802 U | 7/1991 |
| CN | 2279549 Y | 4/1998 |

(Continued)

*Primary Examiner* — Christine H Matthews
(74) *Attorney, Agent, or Firm* — McGlew and Tuttle, P.C.

(57) ABSTRACT

An air humidifier for generating humidified breathing air for a patient includes a boiling pot for receiving a defined water volume. The air humidifier has a partition, the partition having at least one perforation. The partition with perforation is designed to be arranged above a water surface of the defined water volume in the boiling pot.

13 Claims, 4 Drawing Sheets

(56) References Cited

U.S. PATENT DOCUMENTS

| | | | | |
|---|---|---|---|---|
| 6,090,036 | A * | 7/2000 | Kobayashi | A61G 11/00 600/22 |
| 6,115,539 | A * | 9/2000 | Cohn | F24F 6/025 392/402 |
| 2004/0020487 | A1 * | 2/2004 | Koch | A61M 16/162 128/203.12 |
| 2004/0215052 | A1 | 10/2004 | Kullik et al. | |
| 2006/0131764 | A1 * | 6/2006 | Weon | F24F 6/02 261/81 |
| 2006/0163756 | A1 * | 7/2006 | North | F24F 3/14 261/110 |
| 2009/0229360 | A1 * | 9/2009 | Harvey | G01F 19/00 73/427 |
| 2012/0312298 | A1 * | 12/2012 | Humes | A61M 16/10 128/200.13 |

FOREIGN PATENT DOCUMENTS

| | | |
|---|---|---|
| DE | 93 07 380 U1 | 7/1993 |
| DE | 102 34 811 C1 | 11/2003 |
| DE | 10 318 384 B4 | 11/2007 |
| DE | 10 2008 050 240 A1 | 4/2009 |
| DE | 10 2008 016 762 B3 | 9/2009 |

\* cited by examiner

AIR HUMIDIFIER WITH BOIL-OVER PROTECTION

CROSS REFERENCE TO RELATED APPLICATIONS

This application claims the benefit of priority under 35 U.S.C. §119 of German Patent Application DE 10 2012 024 401.0 filed Dec. 13, 2012, the entire contents of which are incorporated herein by reference.

FIELD OF THE INVENTION

The present invention pertains to an air humidifier for generating humidified breathing air for a patient in an incubator with such an air humidifier, a respiration system with such an air humidifier and a method for manufacturing an air humidifier.

BACKGROUND OF THE INVENTION

Air humidifiers, which may be part of a respiration system or of an incubator for supplying premature and newborn babies, are known for humidifying the breathing air for a person. An incubator, which describes a moistener (wherein the terms "moistener" and "air humidifier" are used synonymously in this application) for supplying the patient located in the interior of the incubator with moist breathing air, is described, for example, in DE 103 18 384 B4. However, air humidifiers for generating humidified breathing air are limited to medical purposes, but the present invention also comprises air humidifiers for non-medical purposes.

A moistener is described, for example, in DE 10 2008 016762 B3. The moistener described has a boiling apparatus, which heats water and generates water vapor, which is fed to the patient.

SUMMARY OF THE INVENTION

An object of the present invention is to provide an improved air humidifier.

In one aspect, the present invention pertains to an air humidifier for generating humidified breathing air for a patient (or user in the case of a non-medical application of the air humidifier) with a boiling pot for receiving a defined water volume, and a partition with aperture (a perforated partition/diaphragm), wherein the partition has at least one perforation and is designed such as to be arranged above a water surface of the defined water volume in the boiling pot.

The basic idea of the present invention is that boiling over of the boiling water volume in the boiling pot can be prevented or reduced by the use of a partition with one or more aperture (one or more opening/orifice/perforation). The partition with aperture is arranged above the water level such that a foam layer being formed on the water surface of the boiling water volume can pass through the perforation of the partition with aperture. It is achieved, according to the present invention, that the discharge of liquid from the air humidifier and thus entry of liquid into the patient space of an incubator or the respiration system of a patient due to the boiling-over or the foaming of the water of the water volume being heated in the boiling pot can be prevented or reduced, because if the water being heated in the boiling pot is brought to a boil, it may tend to boil over or foam over, depending on the design of the boiling pot and the degree of contamination of the water. Such boiling-over or foaming-over water may lead to the entry of hot water into the patient space of the incubator or the respiration system of the patient and also to damage to other units of the incubator or respiration system. Liquid is prevented from discharging from the air humidifier by a self-inhibiting foam barrier, which will be explained below, being built up by means of the partition with aperture.

The following effects are achieved by the use of the partition with aperture according to the present invention in a boiling pot: If the water present in the boiling pot is heated, foam and vapor bubbles, which will gradually form a bubble mat, are formed on the water surface. The bubbles gradually rise through the perforation of the partition with aperture into the part of the boiling pot located above the partition with aperture. The bubbles cool above the partition with aperture and form a thin water layer on the partition with aperture. This thin water layer initially flows through the perforation of the partition with aperture back into the lower part of the boiling pot. However, once a certain thickness or height of the water layer has formed above the partition with aperture, this closes the perforation of the partition with aperture, so that the boiling process comes to an end in the lower part of the boiling pot and the water of the water layer above the partition with aperture again flows back into the lower part of the boiling pot. Foaming begins again, so that the bubble mat and the water layer above the partition with aperture will build up and subside in a pulse-like manner.

If the heating output is increased in the boiling pot, the formation of vapor bubbles and foam formation are intensified to the extent that a water layer, which is permanently closed during the boiling process, will be formed above the partition with aperture, and this water layer will not flow back completely into the lower part of the boiling pot any more. The pressure will consequently rise under the partition with aperture and the boiling point will be correspondingly increased.

The vapor bubbles rise from the lower part of the boiling pot through the water layer and are cooled and consequently liquefied in this water layer, on the one hand, and mechanically blocked, on the other hand. Foaming of the cooled, no longer boiling water of the water layer above the partition with aperture occurs to a very greatly reduced extent at best. The discharge of liquid caused by vapor and foam bubbles can thus be reduced or prevented according to the present invention by forming a closed water layer above the partition with aperture.

Another advantage according to the present invention is that the boiling pot can be made smaller or more compact, because foaming over or boiling over is reduced or prevented by means of the use of the partition with aperture. A compact mode of construction of an air humidifier according to the present invention is particularly advantageous especially for portable incubators and portable respiration systems.

In one embodiment, the aperture/opening/orifice/perforation or the plural apertures/openings/orifices/perforations of has/have an area of 50 mm$^2$ to 120 mm$^2$. In a preferred embodiment, the aperture/opening/orifice/perforation or the plural apertures/openings/orifices/perforations of has/have an area of 70 mm$^2$ to 90 mm$^2$. In an especially preferred embodiment, the aperture/opening/orifice/perforation has, for example, a diameter of 10 mm and is round and is located in the center of the partition with aperture. Foaming over or boiling over of vapor and foam bubbles from an air humidifier can be reduced especially well according to the present invention if the perforation has an area of 50 mm$^2$ to 120 mm$^2$. However, these data are related to preferred embodiments only, and the present invention is not limited to the areas indicated. The perforation area with which an especially good reduction of foaming over or boiling over can be achieved rather depends on the size of the vapor bubbles and foam bubbles, the boiling water volume, the degree of contamination of the water, the size of the boiling apparatus, the pressure and temperature in the air humidifier. If the perforation of the partition with aperture is too large, no closed water layer can develop above the partition with aperture and the partition with aperture loses its effect. If the perforation is too small, the quantity of vapor generated in the air humidifier will be too small to sufficiently humidify the breathing air of the person and an undesired noise may be generated. If the quantity of vapor that passes through the relatively small perforation is to be increased, the energy supply must be increased in the lower part of the boiling pot, as a result of which the pressure is increased at the same time, which may lead to undesired side effects on other functional parts of the air humidifier, for example, the water feed unit and the water level regulating means. As was already mentioned above, a perforation area of 70 mm$^2$ to 90 mm$^2$ has proved to be especially advantageous.

In one embodiment, the perforation (the aperture/opening/orifice/perforation) of the partition with aperture according to the present invention is round and has a diameter of 8 mm to 12 mm and especially preferably a perforation diameter of 9.5 mm to 10.5 mm. However, the perforation of the partition with aperture may also have a rectangular, triangular, oblong, semicircular or any other shape. Furthermore, the partition with aperture may also have a plurality of apertures/openings/orifices/perforations, which may have any shape whatsoever. The perforation may be arranged in a central area or even in a non-central area of the partition with aperture.

In one embodiment, the partition with aperture is designed to be arranged essentially in parallel with a water surface of the defined water volume. Such a partition with aperture can be arranged essentially at right angles to the inner wall of the boiling pot. The partition with aperture may be arranged in the boiling pot, for example, by a clamping fixation on a round projection of the inner wall of the boiling pot or on a plurality of projections of the inner wall of the boiling pot. However, the partition with aperture may also be arranged at an angle not equaling 90° in relation to the inner wall of the boiling pot and consequently sloped in relation to the water surface in an alternative embodiment. The partition with aperture is fixed on the inner wall of the boiling pot in a preferred embodiment.

The partition with aperture is of a funnel-shaped design in one embodiment. In such an embodiment, the partition with aperture may be arranged in its middle (i.e., central) area closer to or farther away from the water surface than an outer edge area of the partition with aperture. The central part of the funnel-shaped partition with aperture located closest to the water surface has the perforation according to the present invention in a preferred embodiment. The flowing back of the water layer is supported by the geometric shape of a funnel-shaped partition with aperture, so that a stable state of the closed water layer can become established above the partition with aperture in the boiling pot especially rapidly.

In one embodiment, the air humidifier has, furthermore, a heating element for heating the defined water volume in the boiling pot. The heating element may be arranged above the boiling pot or it may even be arranged around the boiling pot or integrated in the inner wall thereof in order to make an especially compact mode of construction possible.

In one embodiment, the air humidifier has a water tank and/or the boiling pot has a mark for determining the defined water volume. The water volume to be heated in the boiling pot can be determined, for example, by a water tank arranged essentially next to the boiling pot feeding fresh water to the boiling pot as soon as the water level in the boiling pot drops due to evaporation of the boiling water. It is also possible that the boiling pot has a mark for determining the defined water volume up to which the boiling pot is filled with water by a user of the air humidifier.

In one embodiment, the air humidifier has a water/vapor housing part (spout) with a vapor outlet, wherein said housing part or spout is designed to be connected with a respiration system and/or incubator.

In one embodiment, the partition with aperture is arranged at a distance of 1 cm to 4 cm and preferably 2 cm to 3 cm above the water level of the defined water volume. The partition with aperture is arranged 2.5 cm above the water level of the defined water volume in an especially preferred embodiment. Furthermore, it is preferred that the partition with aperture be arranged approximately centrally between a vapor outlet of the air humidifier and the water surface of the defined water volume.

In another aspect, the present invention pertains to an incubator with an air humidifier according to the present invention, with a patient space with a reclining surface for accommodating a patient, and with a breathing air feed means for feeding the moistened breathing air into the patient space. The incubator may be designed as a closed incubator or as an open care unit. The incubator may be designed, furthermore, as a stationary or portable unit.

In another aspect, the present invention pertains to a respiration system with an air humidifier in accordance with the invention and with a breathing air feed means for feeding the moistened breathing air to a patient or to a user of the respiration system. In particular, the respiration system according to the present invention is not limited to medical purposes, but it may also be used in industrial or safety engineering areas, in which an air humidifier is advantageous for the breathing air of the user.

In another aspect, the present invention pertains to a method for manufacturing an air humidifier with the steps of providing a boiling pot for receiving a defined water volume, providing a partition with aperture with at least one perforation, and arranging the partition with aperture in the boiling pot above a water surface of the defined water volume. It should be noted in this connection that the partition with aperture may be arranged in the boiling pot by the manufacturer or by the user. The partition with aperture may be designed, for example, according to the present invention to be arranged replaceably in the boiling pot in order to make easy cleaning of the boiling pot possible and to meet hygienic requirements by regularly replacing the partition with aperture. The scope of the present invention consequently also covers an air humidifier kit, which has a boiling pot for receiving a defined water volume, which said boiling pot is designed to receive a partition with aperture in the interior of the boiling pot, and the kit has, furthermore, at least one additional partition with aperture, which is designed to be arranged in the boiling pot.

The above-described embodiments may be combined with one another and with the above-described aspects as desired to obtain advantages according to the present invention.

Preferred combinations of above-described embodiments will be described as examples below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
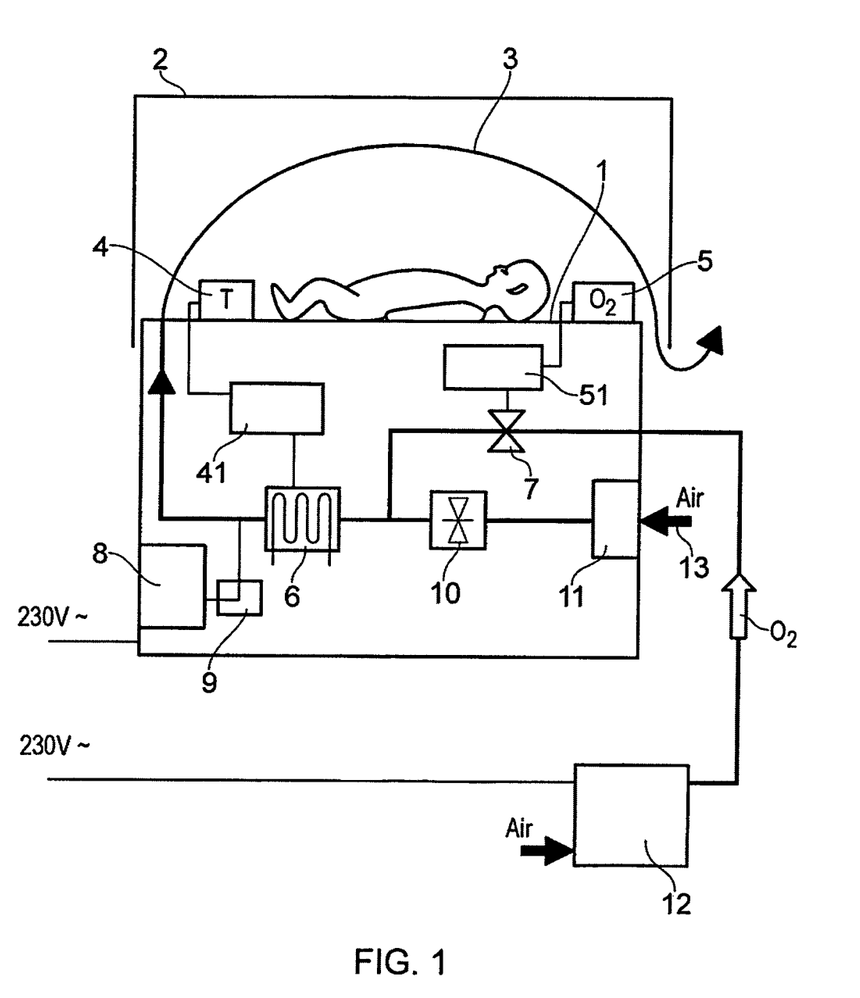
FIG. 1 is a schematic view showing an incubator with an air humidifier according to one embodiment of the present invention.

Referring to the drawings in particular, FIG. 1 shows an embodiment of an incubator, which has an air humidifier according to an embodiment of the present invention. A reclining surface 1 for a patient is arranged under the incubator hood 2. The interior space of the incubator is supplied by a fresh gas stream 3 with fresh gas or breathing air for the patient. To ensure a sufficient inflow of oxygen under the incubator hood 2, an oxygen sensor 5 measures the oxygen content in the interior space of the incubator and sends the measurement result to an oxygen regulator 51. The oxygen regulator 51 actuates the oxygen dispenser 7, which regulates the content of oxygen, which is fed to the system via the oxygen concentrator 12.

The fresh gas stream 3 fed into the interior space of the incubator has a portion of the gas stream sent through the oxygen concentrator 12 and the oxygen dispenser 7 as well as a portion of a fresh air stream 13, which are delivered through a microorganism filter 11 and a blower 10. The combined fresh gas stream 3 is sent subsequently through a heater 6, which heats the fresh gas stream such as this is measured by the temperature sensor 4 as being necessary and regulated by the temperature regulator 41.

The fresh gas stream enriched with oxygen, which has passed through the heater 6, is subsequently enriched with moisture before it is sent into the interior space of the incubator. A moistener 9 (which is shown schematically in FIG. 1 and is also called "air humidifier" in the present application), which is connected with a water tank 8, from which fresh water is sent into the boiling pot evaporating water vapor, is provided for humidifying the breathing air.

Figure 2A:
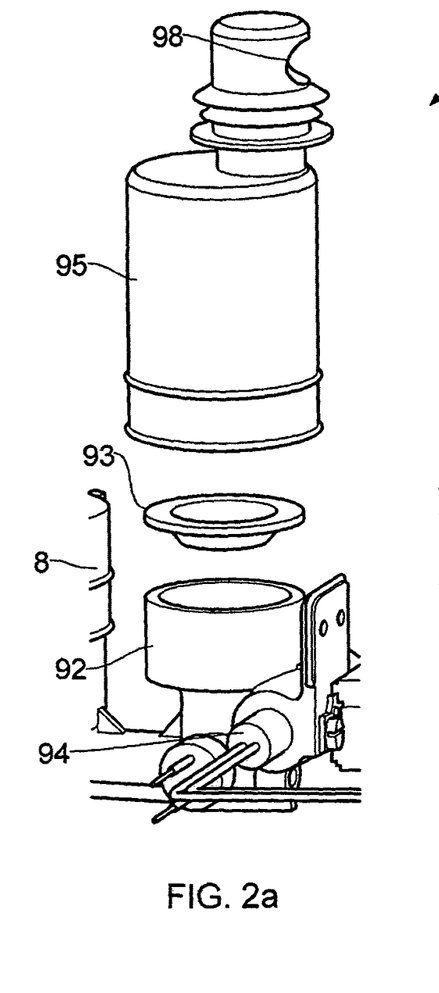
FIG. 2a is an exploded perspective view showing an embodiment of an air humidifier according to the present invention.
Figure 2B:
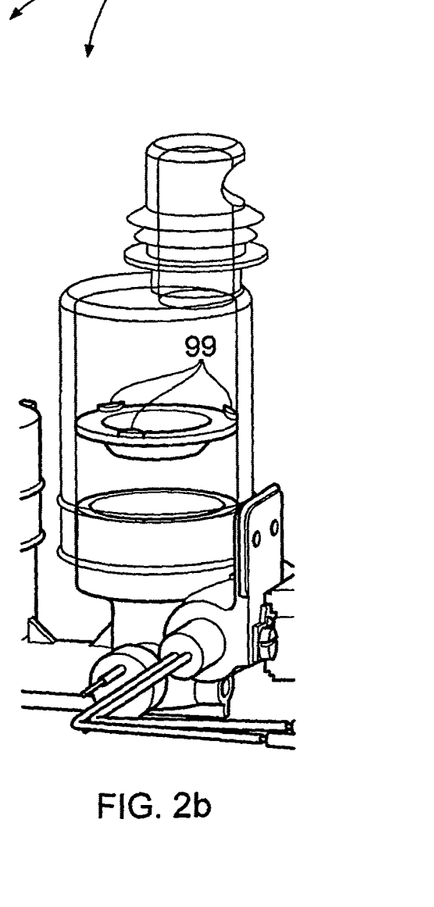
FIG. 2b is a perspective view showing the embodiment of an air humidifier according to FIG. 2a with a housing part (spout) shown as a transparent housing part.
Figure 2C:
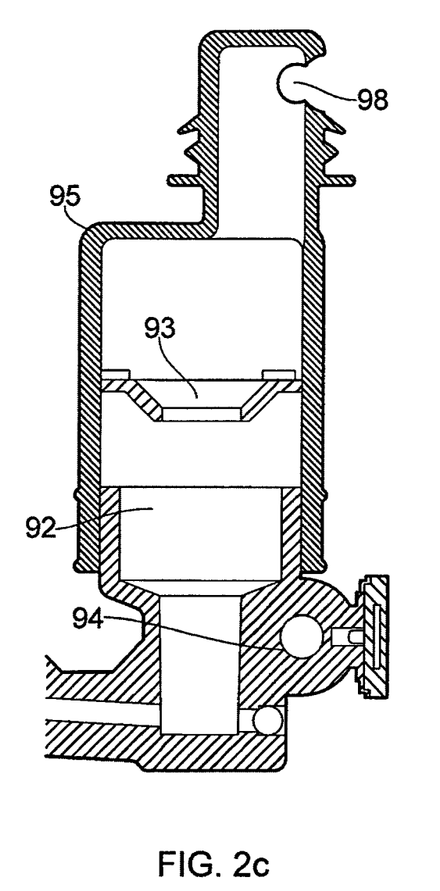
FIG. 2c is a sectional view showing the embodiment of an air humidifier according to FIG. 2b with the housing part (spout) not shown as a transparent housing part.
Figure 2D:
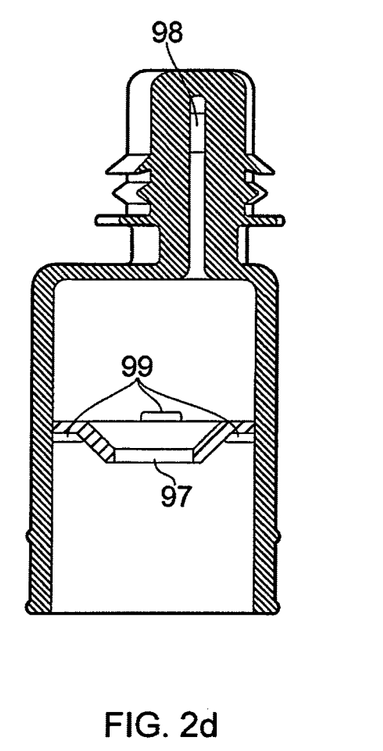
FIG. 2d is another sectional view showing the embodiment of an air humidifier according to FIG. 2b with the housing part (spout) not shown as a transparent housing part.

FIGS. 2a through 2d show views of an embodiment of an air humidifier according to the present invention. FIG. 2a shows an embodiment of an air humidifier 90 before mounting and FIG. 2b shows the embodiment of an air humidifier 90 after mounting, with a housing part 95 being shown as a transparent housing part in FIG. 2b in order to make a view into the interior of the air humidifier 90 possible. FIG. 2c shows a cross section through the air humidifier 90 according to FIG. 2b with non-transparent housing part 95. FIG. 2d shows another perspective view of a cross section through the air humidifier 90 according to FIG. 2b with non-transparent housing part 95.

The air humidifier 90 (which corresponds, for example, to the moistener 9) has a boiling pot (boiling pot housing part) 92 for receiving a defined water volume. A water tank 8 feeds fresh water to the boiling pot 92, so that an essentially constant defined water volume 91 (not shown in FIG. 2) is always present in the boiling pot 92. An especially hygienic humidification of the breathing air is achieved by feeding fresh water from the water tank 8, which is boiled off at first in the boiling pot 92 before it is fed as vapor to the breathing air. A partition with aperture 93 is arranged above the water surface of the water volume 91. In one embodiment, the boiling pot has, for example, a diameter of 35 mm and the defined water volume 91 equals 10 cm3. The boiling pot 92 adjoins a vapor space housing part (spout housing part) 95, which can be connected with a respiration system or an incubator. The housing part 95 has a vapor outlet 98, through which the water vapor can be fed to the respiration system or incubator.

The air humidifier 90 has, furthermore, a heating element 94, which is arranged on one side of the boiling pot 92 and which heats the water contained in this. The partition with aperture 93 is fixed to the inner wall of the boiling pot 92 by means of between projections 99 on the inner wall of the boiling pot, which act as fixing means. The partition with aperture 93 of the embodiment shown in FIG. 2 is funnel-shaped and has a central perforation 97.

FIGS. 3a through 3d show another embodiment of an air humidifier according to the present invention, which differs from the embodiment according to FIG. 2 essentially in that the partition with aperture 93 is flat (i.e., not funnel-shaped). Insofar as the features of the air humidifier 93 according to FIG. 3 are essentially identical to those in FIG. 2, reference is made to the above description.

It will be explained blow on the basis of FIGS. 3a through 3d how an embodiment of a partition with aperture prevents or reduces foaming over or boiling over.

Figure 3A:
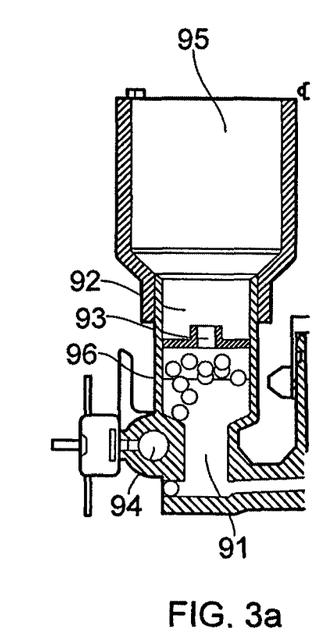
FIG. 3a is a sectional view of another embodiment of an air humidifier according to the present invention showing a mode of operation.

FIG. 3a shows a boiling pot 92 with gently boiling water 91 and a low level of contamination. The heating output of the heating element 94, which is designed, for example, as a cartridge type heater, leads to the formation of vapor bubbles, as is indicated in FIG. 3a.

Figure 3B:
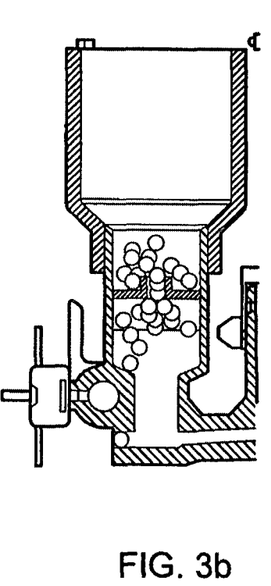
FIG. 3b is a sectional view of the embodiment of FIG. 3a, showing another mode of operation.

More foam or vapor bubbles will gradually form due to further heating of the eater 91, and they will eventually escape through the diaphragm opening; this is shown in FIG. 3b.

The bubbles passing through the perforation 97 of the partition with aperture 93 will cool down above the partition with aperture 93 and come to lie as a thin film of water on the partition with aperture 93. If the perforation 97 of the partition with aperture 93 is closed by the water layer formed, the boiling process in the lower part of the boiling pot 92 will come to an end in a short time until the water of this water layer has flowed back into the lower part of the boiling pot 92. The formation of rising bubbles and of the water layer begins anew. A pulse-like build-up and subsiding can be recognized.

Figure 3C:
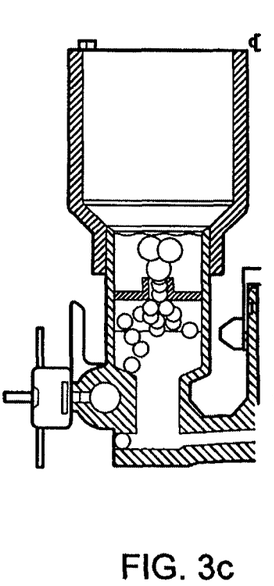
FIG. 3c is a sectional view of the embodiment of FIG. 3a, showing another mode of operation.
Figure 3D:
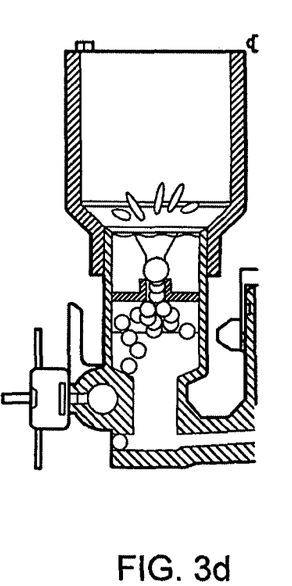
FIG. 3d is a sectional view of the embodiment of FIG. 3a, showing another mode of operation.

By increasing the heating output, the formation of vapor bubbles and vapor foam is increased such that a closed water layer can eventually form on the partition with aperture 93, and this water layer cannot flow back completely into the lower part of the boiling pot 92 any longer, as this is shown in FIGS. 3c and 3d. As a consequence, the pressure rises under the partition with aperture 93, which can also be measured as an increase in the boiling point. Bubbles will continue to rise through the water layer with the increased pressure, but these bubbles will burst in this [water layer]. Foaming above the water layer is thus prevented or reduced by the slightly cooled, no longer boiling water.

While specific embodiments of the invention have been shown and described in detail to illustrate the application of the principles of the invention, it will be understood that the invention may be embodied otherwise without departing from such principles.

APPENDIX

List of Reference Numbers

1 Reclining surface
2 Incubator hood
3 Fresh gas stream
4 Temperature sensor
5 Oxygen sensor
6 Heater
7 Oxygen dispenser
8 Water tank
9 Moistener
10 Blower
11 Microorganism filter
12 Oxygen concentrator
13 Fresh air stream
41 Temperature regulator
51 Oxygen regulator
90 Air humidifier
91 Water volume
92 Boiling pot
93 Partition with aperture
94 Heating element
95 Housing part
96 Mark
97 Perforation/aperture/opening
98 Vapor outlet
99 Fixing means

What is claimed is:

1. An air humidifier for generating humidified breathing air for a patient, the air humidifier comprising:
a housing comprising a boiling pot with a water feed inlet, the boiling pot receiving a defined water volume with a water surface and with an upper housing portion defining a vapor space situated adjacent to and above the boiling pot and with a vapor space vapor outlet, wherein during operation only fluid from the boiling pot is present in the vapor space and only fluid released from the vapor space passes through the vapor outlet; and
a partition having at least one perforation allowing liquid and vapor to pass through the at least one perforation from below the partition to above the partition, the partition being arranged above the water surface of the defined water volume in the boiling pot and below at least a portion of the vapor space and below the vapor outlet, wherein the partition is funnel-shaped.

2. An air humidifier in accordance with claim 1, wherein the at least one perforation has an area of 50 mm$^2$ to 120 mm$^2$.

3. An air humidifier in accordance with claim 1, wherein the at least one perforation has an area of 70 mm$^2$ to 90 mm$^2$.

4. An air humidifier in accordance with claim 1, wherein the at least one perforation is round and has a diameter of 8 mm to 12 mm.

5. An air humidifier in accordance with claim 1, wherein the at least one perforation is round and has a diameter of 9.5 mm to 10.5 mm.

6. An air humidifier in accordance with claim 1, further comprising a heating element connected to the housing for heating the defined water volume in the boiling pot.

7. An air humidifier in accordance with claim 1, further comprising a water tank with a water feed operatively connected to the water feed inlet and feeding fresh water to the boiling pot and maintaining an essentially constant said defined water volume, wherein the boiling pot has a mark or indication for determining the defined water volume.

8. An incubator comprising:
an air humidifier for generating humidified breathing air for a patient, the air humidifier comprising a housing comprising a boiling pot with a water feed inlet, the boiling pot receiving a defined water volume with a water surface and with an upper housing portion defining a vapor space situated adjacent to and above the boiling pot and with a vapor space vapor outlet, wherein during operation only fluid from the boiling pot is present in the vapor space and only fluid released from the vapor space passes through the vapor outlet and a partition with at least one perforation allowing liquid fluid and gaseous fluid passage through the at least one perforation from below the partition to above the partition, the partition being arranged above the water surface of the defined water volume in the boiling pot and below at least a portion of the vapor space and below the vapor outlet;
a patient space with a reclining surface for a patient for accommodating the patient; and
a breathing air feed means for feeding the humidified breathing air to the patient space, the breathing air feed means comprising a gas line with an environmental air inlet and a humidified air outlet and further comprising a blower for moving gas within the gas line in a direction from the air inlet toward the humidified air outlet, the vapor outlet being connected to the gas line between the air inlet and the humidified air outlet to feed vapor from the vapor space into the gas line to add vapor to environmental air to form the humidified air.

9. An incubator in accordance with claim 8, wherein the at least one perforation has an area of 50 mm$^2$ to 120 mm$^2$.

10. An incubator in accordance with claim 8, wherein the at least one perforation is round and has a diameter of 8 mm to 12 mm.

11. An incubator in accordance with claim 8, wherein the partition is funnel-shaped.

12. An incubator in accordance with claim 8, further comprising a heating element connected to the housing for heating the defined water volume in the boiling pot.

13. An incubator in accordance with claim 8, further comprising a water tank with a water feed operatively connected to the water feed inlet and feeding fresh water to the boiling pot and maintaining an essentially constant said defined water volume, wherein the boiling pot has a mark or indication for determining the defined water volume.

* * * * *